United States Patent [19]

Wuest et al.

[11] Patent Number: 5,318,709
[45] Date of Patent: Jun. 7, 1994

[54] PROCESS FOR THE PRODUCTION OF SURFACTANT MIXTURES BASED ON ETHER SULFONATES AND THEIR USE

[75] Inventors: Willi Wuest, Ratingen; Rainer Eskuchen, Duesseldorf; Bernd Richter, Leichlingen, all of Fed. Rep. of Germany

[73] Assignee: Henkel Kommanditgesellschaft auf Aktien, Fed. Rep. of Germany

[21] Appl. No.: 778,116

[22] PCT Filed: May 28, 1990

[86] PCT No.: PCT/EP90/00855

§ 371 Date: Dec. 5, 1991

§ 102(e) Date: Dec. 5, 1991

[87] PCT Pub. No.: WO90/15050

PCT Pub. Date: Dec. 13, 1990

[30] Foreign Application Priority Data

Jun. 5, 1989 [DE] Fed. Rep. of Germany ....... 3918265

[51] Int. Cl.$^5$ ............... E21B 43/22; C07C 309/09; C07C 303; C07C /02; C07C 303/32

[52] U.S. Cl. .................. 252/8.554; 562/42; 562/110

[58] Field of Search ............... 562/42, 110; 252/8.554

[56] References Cited

U.S. PATENT DOCUMENTS 3,827,497  8/1974  Dycus et al. ............... 252/8.554 X
4,784,801  11/1988  Hoeffkes et al. ................ 252/554

*Primary Examiner*—Gary Geist
*Attorney, Agent, or Firm*—Ernest G. Szoke; Wayne C. Jaeschke; Real J. Grandmaison

[57] ABSTRACT

A process for the production of a surfactant mixture for use in enhanced oil recovery wherein the surfactant mixture comprises an alkyl ether sulfonic acid or salt thereof as a principal constituent and at most a substantially equal quantity of alkoxylated alcohol. The surfactant mixture is prepared by reacting an alkyl ether sulfate with a stoichiometric excess of an alkali metal sulfite solution at about 160° C. to 220° C. under mildly alkaline pH conditions, and then extracting sulfate salt therefrom using a substantially water-insoluble alcohol at a lowered temperature.

6 Claims, No Drawings

PROCESS FOR THE PRODUCTION OF SURFACTANT MIXTURES BASED ON ETHER SULFONATES AND THEIR USE

BACKGROUND OF THE INVENTION

1. Field of the Invention

This invention relates to a new process for the production of surfactants and surfactant mixtures based on fatty alcohol ether sulfonates which enables this industrially interesting class of surfactants to be economically obtained.

2. Discussion of Related Art

Enhanced oil recovery, in which the quantities of residual oil retained in the reservoir by viscosity and capillary effects in the pore space are made at least partly recoverable, is acquiring increasing interest. Many types of process have been proposed for enhanced oil recovery, including for example polymer flooding, alkali flooding, thermal processes or solution flooding.

The present invention is concerned with the process known as surfactant flooding. Whereas, in the fresh oil reservoir, the oil is present as continuous phase in the rock pore space, the oil phase disintegrates with increasing primary and secondary recovery into individual discrete droplets which are retained in narrow pores under the effect of the high interfacial tension. Overcoming the capillary forces either requires extremely high pressures or a considerable reduction in the interfacial tension between water and oil using suitable surfactants. In each individual case, this reduction depends to a very large extent on the reservoir temperature, the salinity of the reservoir water and the composition of the oil. The desired so-called middle phase micro-emulsion—a central third phase between the heavier salt water phase and the lighter oil phase—is only formed through adaptation of the particular surfactant mixture and under the conditions of the extreme reduction in interfacial tension. The formation of the middle phase micro-emulsion is crucially important to the recovery of residual oil.

Suitable surfactants have to satisfy various requirements over and above their ability to reduce interfacial tension to a considerable extent. For example, they must not form any deposits in the flood water or formation water because otherwise there would be a danger of irreversible blockage in the reservoir. They should be adsorbed to the rock to only a minimal extent, if at all. They should be stable under reservoir conditions, remaining stable for periods of 1 to 3 years for distances between the injection probe and the recovery probe of 50 to 300 m and flooding rates of approx. 0.3 m/d.

Ether sulfates, ether carboxylates, ether sulfonates and ether phosphates in particular have been proposed as surfactants for use in high-salinity reservoir waters. Ether sulfates and ether phosphates are readily obtainable on an industrial scale, but lack stability to hydrolysis. Ether sulfonates and, more particularly, alkyl ether sulfonates have shown particularly interesting properties in screening tests. They combine high electrolyte compatibility with high stability to hydrolysis at high temperatures. In particular, however, they also show the appearance of the desired three-phase states in the oil/water/surfactant systems with a broad middle phase micro-emulsion range and a pronounced reduction in interfacial tension. Mixtures of these surfactants with other surfactants and/or so-called co-solvents open up technically interesting possibilities in the field of enhanced oil recovery.

Numerous syntheses have been proposed for the preparation of ether sulfonates, cf. for example the Article entitled "Fettalkoholethersulfonate für die tertiäre Erdölförderung (Fatty Alcohol Ether Sulfonates for Enhanced Oil Recovery)" in Fette-Seifen-Anstrichmittel, 1985, 382–385 and the literature cited therein. The problem addressed by the present invention was to provide a technologically simple process which would enable this interesting class of surfactants to be economically produced and which, in particular, would provide as a direct reaction product a surfactant-containing multicomponent mixture which would have valuable properties as such for the stated application. This primary surfactant mixture would consist of the abovementioned alkyl ether sulfonates as the desired main component and, in addition, would contain nonionic fatty alcohol ethers forming the basis of the ether sulfonates and, optionally, so-called co-solvents based on synthetic and/or natural alcohols.

DESCRIPTION OF THE INVENTION

Other than in the operating examples, or where otherwise indicated, all numbers expressing quantities of ingredients or reaction conditions used herein are to be understood as modified in all instances by the term "about".

In a first embodiment, therefore, the present invention relates to a process for the production of surfactant mixtures based on alkyl ether sulfonic acids or salts thereof (ether sulfonates) as principal constituent which may be used in particular in enhanced oil recovery and are obtained by reaction of alkyl ether sulfates with an aqueous alkali metal sulfite solution at temperatures of 160° to 220° C., this process being characterized in that, to prepare mixtures—at least substantially free from sulfate salt—of the ether sulfonates based on alkoxylated alcohols of natural and/or synthetic origin with at most substantially equal quantities of the alkoxylated alcohols, the reaction is carried out with a stoichiometric excess of alkali metal sulfite in aqueous medium at a mildly alkaline pH value, the reaction mixture is optionally left to continue reacting under the described reaction conditions and the surfactant mixture formed is extracted with at least substantially water-insoluble alcohols at reduced, but still elevated temperatures.

In another embodiment, the invention relates to the surfactant mixtures produced by this process, more particularly in admixture with residual alcohol from the extraction stage for tertiary oil recovery.

It is known that the alkoxylation of alcohols of natural and/or synthetic origin, particularly fatty alcohols, with ethylene oxide and/or propylene oxide gives correspondingly alkoxylated fatty alcohol compounds resembling nonionic surfactants in character. Their terminal esterification with sulfuric acid to form the corresponding sulfate salts gives the fatty alcohol sulfates.

In the type of process with which the present invention is concerned, the alkyl ether sulfates are reacted in a nucleophilic substitution with sulfite to form the alkyl ether sulfonate which is referred to more simply hereinafter as "ether sulfonate". The associated reaction equation of the desired main reaction is as follows:

$$R'\text{---}O\text{---}SO_3Na + Na_2SO_3 \rightarrow R'\text{---}SO_3Na + Na_2SO_4 \qquad (I)$$

In this equation, R' corresponds to the alkoxylated alcohol radical.

The nucleophilic substitution in question requires comparatively high temperatures and correspondingly high pressures, but is nevertheless a comparatively slow reaction. This reaction, which is carried out in aqueous medium, results in the formation of considerable quantities of alkoxylated alcohol as saponification product, normally resembling a nonionic surfactant in character. At the same time, however, the following additional consideration is crucial to the application of the surfactants formed in accordance with the invention:

The sodium sulfate accumulating in aqueous phase as a secondary reaction product must have been almost completely removed from the surfactant mixture to be ultimately separated off. If, in practical application, substantial quantities of the sulfate anion were to be introduced into the oil reservoir through the surfactant components thus formed, the capillary system would become rapidly blocked by the in situ formation of alkaline earth metal sulfates. Accordingly, the type of reaction in question for the formation of the ether sulfonates involves a very much more complex problem for the practical and economic production of suitable surfactants or surfactant mixtures than originally appeared to be the case. The situation is additionally complicated by the fact that the reaction of the ether sulfates with sodium sulfite in aqueous solution is not without problems. The reaction mixtures tend to gel so that they are difficult to handle and, at the high reaction temperatures required, quickly form crust-like deposits on the inner walls of the reactor so that the reaction has to be interrupted to clean the interior of the reactor.

The teaching according to the invention as described in the following encompasses two problem areas which are solved by the measures taken in accordance with the invention in such a way that surfactants or surfactant mixtures of the type in question can be produced on an industrial scale.

The first problem area concerns the sum total of measures which lead to optimization of the nucleophilic substitution reaction illustrated by the above equation. The second problem area concerns the removal and purification of the valuable product formed from the reaction mixture. The following observations may be made in this regard:

The Nucleophilic Substitution

The preferred starting materials on the alkyl ether sulfate side are corresponding components containing at least predominantly 6 to 18 carbon atoms and, more particularly, 10 to 16 carbon atoms in the alkyl group of the alcohol. Alcohols or mixtures of alcohols containing on average 12 to 14 carbon atoms in the molecule are particularly suitable as the basis of the class of surfactants in question. Suitable alcohols are of both natural and synthetic origin; mixtures of such alcohols may also form the basis of the compounds in question. Suitable natural starting materials for the production of the alkyl ether sulfates, which is not being claimed, are for example corresponding coconut oil and/or palm kernel oil fatty alcohols which have been obtained by hydrogenating reduction of the fatty acids or fatty acid methyl esters. The alcohols on which the alkyl ether sulfates are based are preferably saturated compounds, but if desired may also be olefinically unsaturated.

The alcohols used as principal starting material in the production of the alkyl ether sulfates are alkoxylated, ethylene oxide and/or propylene oxide in particular being used in known manner for the alkoxylation of the alcohols. In the preferred embodiment, the corresponding fatty alcohol alkoxylates have an average degree of alkoxylation above 1 and preferably not more than 10, particularly suitable average degrees of alkoxylation being between above 2 and 8. The HLB values of the nonionic surfactant components formed are determined in known manner by the length of the C chain distribution and the degree of alkoxylation. The alkyl ether sulfates used as one of the key reactants in the process according to the invention are formed by esterification of the alkyl ethoxylates with sulfuric acid, the corresponding sodium salts generally being introduced into the reaction according to the invention in aqueous solution. It has been found in this regard that 10 to 40% by weight aqueous solutions and, more particularly, 15 to 25% by weight aqueous solutions of the ether sulfates may be used with particular advantage. According to the invention, however, it is also possible to use considerably more concentrated solutions, for example approximately 70% by weight solutions, of the ether sulfates. The other reactant for the nucleophilic substitution reaction is sodium sulfite which is also introduced in aqueous solution. The sodium sulfite may be used as such although it is also possible in accordance with the invention to use the less expensive sodium disulfite ($Na_2S_2O_5$) to save costs. It is known that $Na_2S_2O_5$ forms the following equilibrium in aqueous solution in the presence of a base which, according to the invention, is preferably sodium hydroxide:

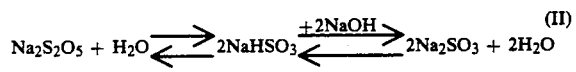

(II)

$$Na_2S_2O_5 + H_2O \rightleftharpoons 2NaHSO_3 \xrightleftharpoons[]{+2NaOH} 2Na_2SO_3 + 2H_2O$$

According to the invention, the alkali metal sulfite is used in a stoichiometric excess in the reaction. A preferred upper limit to this stoichiometric excess is at a molar ratio of sulfite to ether sulfate of about 5, the preferred lower limit being at about 1.5. A stoichiometric sulfite excess of about 1.5 to 3 mol per mol alkyl ether sulfate is particularly suitable.

Another preferred embodiment of the invention is concerned with the predetermined direction in which the reactant solutions to be reacted with one another are added. In the more important embodiment of the invention where the process is carried out in batches, the aqueous alkali metal sulfite is introduced first under the reaction conditions. The aqueous alkyl ether sulfate solution is introduced into the sulfite solution, best with simultaneous mixing. More particularly, the alkyl ether sulfate solution is added in batches or preferably continuously at such a slow rate that a considerable proportion of the total reaction time selected is required for the introduction of the alkyl ether sulfate. In the preferred embodiment, at least about 20% of the total reaction time required is taken up by this addition.

In another preferred embodiment, the concentration of the reactants is limited so that surfactant contents of not more than about 40% by weight and, more particularly, up to about 25% by weight are established in the aqueous reaction mixture accumulating. The reaction is carried out in a mildly alkaline pH range, more particularly at a pH value of from about 7.5 to 10, "sodium-alkaline" conditions being particularly preferred.

By coordinating the reaction parameters with one another, the reaction can be optimized towards the desired nucleophilic substitution reaction with simultaneous limitation or minimization of the alcohol ethoxylate component, preferably to values below 50% by weight and, more particularly, to values of at most about 30 to 40% by weight, based on the total surfactant content. The particularly preferred process parameters are as follows: Reaction temperatures in the range from about 180° to 200° C., pH values of the reaction mixture in the range from about 8 to 9 and molar ratios of sulfite to alkyl ether sulfate of 1.5 to 2 at pressures of up to about 20 bar, preferably under "natural" pressure.

The surfactant mixtures formed may have alkyl ether sulfonate contents of at least 60% by weight and preferably of at least about 70% by weight. The described choice of the delayed addition of the alkyl ether sulfate reaction component ensures that the unwanted gelation of the reaction mixture and, hence, the formation of crust-like deposits on the inner walls of the reactor are safely prevented. The reaction times are typically between about 2 and 6 hours and preferably at least about 3 hours per reaction batch.

ISOLATION OF THE SURFACTANT MIXTURE FORMED

The ether sulfonates, but preferably the mixture of ether sulfonates and alcohol alkoxylates thus formed has to be separated from the aqueous salt solution in a following step. As already mentioned, it is particularly important in this regard to ensure that the salts dissolved in the aqueous phase only pass over into the surfactant mixture to be separated in small quantities, if at all.

For this separation step, the teaching according to the invention uses a measure of which neither the usefulness nor the effectiveness in the form described hereinafter was foreseeable.

Under carefully selected operating conditions, particularly in regard to the operating temperature, it is possible to achieve substantially quantitative separation of the aqueous salt-containing phase and the surfactant phase formed by extraction with water-insoluble alcohols. At least substantially water-insoluble alcohols of synthetic and/or natural origin preferably containing up to 14 carbon atoms and, more particularly, from 4 to 8 carbon atoms are suitable. Particularly suitable extractants are amyl alcohols and/or hexanols of synthetic and/or natural origin which may be linear and/or branched. The following observations may again be made in this regard:

Extraction with the alcohol phase is carried out in one or more stages, preferably at temperatures of from about 50° to 100° C. and, more preferably, at temperatures of from about 80° to 90° C. Suitable mixing ratios of the reaction mixture to be extracted to the extractant are preferably not more than about 30% by weight and, more particularly, in the range from about 3.5 to 15% by weight. Extraction may be carried out in batches, semicontinuously or even continuously. Simple mixing of the phases to be contacted with one another is sufficient for effective extraction.

On completion of extraction, the aqueous phase and the alcoholic phase generally separate smoothly from one another, the alcoholic phase is removed and is best subjected to further working up.

In the course of this working up, the alcohol used as extractant is preferably at least partly recovered, for example by distillation, and separated from the surfactant mixture formed. The alcohol recovered may be reused in the next extraction phase.

For the purposes of the invention, however, it is particularly important that lower alcohols of the type used herein as extractants, more particularly the preferred $C_{5/6}$ alcohols, are used in practice as so-called co-solvents for enhanced oil recovery. According to the invention, therefore, it is not necessary at all to continue removal of the alcohol to very small residual contents in the surfactant mixture. Instead, the multicomponent surfactant/alcohol mixture still containing considerable proportions of alcohol may be directly used for the intended application. Preferred residual alcohol contents in the reaction product separated off are, for example, contents of up to about 100% by weight, residual alcohol contents of from 15 to 35% by weight, based on the surfactant mixture, being particularly preferred.

The content of troublesome sulfate ions in the reaction mixture thus obtained is typically below 0.5% by weight and best below about 0.2% by weight and may even be kept at a maximum value of about 0.1% by weight. Such low contents of sulfate ions in the surfactant mixture are acceptable for the intended application.

EXAMPLES

I. Starting Materials and Reaction Conditions for Three Typical Pilot Plant Trials (Reaction)

| Starting material | | Trial 1 | Trial 2 | Trial 3 |
|---|---|---|---|---|
| Texapon K 14 S; 25% ($C_{12/14}$ ether sulfate; 3.6 EO) | (kg) | 310.5 | 414.2 | — |
| LS 8 sulfate, 25% ($C_{12/14}$ ether sulfate; 8 EO) | (kg) | — | — | 393 |
| Sodium sulfite | (kg) | 33.9 | 60.0 | 59 |
| Water | (kg) | 86.9 | 101.4 | 249.8 |
| Surfactant content | (%) | 18 | 18 | 14 |
| mol $SO_3^{2-}$ | | 1.5 | 2.0 | 3.0 |
| mol ether sulfate | | | | |
| pH | | 9 | 9 | 9 |
| Reaction temperature | (°C.) | 210 | 200 | 180 |
| Addition time | (h) | 1 | 1 | 1 |
| Reaction time (incl. addition time) | (h) | 5 | 4 | 8 |
| Yield of ether sulfonate | (%) | 72.3 | 76.2 | 78.9 |

II. Starting Materials and Test Parameters for the Extraction Phase

| | Trial 1 | Trial 2 | Trial 3 |
|---|---|---|---|
| Feed | RM* Trial 1 | RM Trial 2 | RM Trial 3 |
| Extractant | + | — | + |
| Hexanol | — | + | — |
| Pentanol (isomer mixture) | — | + | + |
| Process batch continuous | + | — | — |
| Feed Extractant | 3.5 | 10 | 2.3 |

*Reaction mixture

III. Experimental Setup

1. Reaction

The syntheses of the ether sulfonates based on the corresponding ether sulfates were carried out in a 1 m³ pressure reactor with the following technical data;
 Stirred reactor, 1 m³, material 1.4539
 Permitted operating pressure: 30 bar In addition to the heating/cooling surface of the reactor wall, the reactor is equipped with an internal heating coil. 4-Stage slotted Internig mixer with a trapezoidal stirrer as the final element. Piston metering pump for introducing the ether sulfate solution.

2. Extraction

Batch: 1 m³ pressure reactor
Continuous: 3 m extraction limit column; internal diameter 5 cm, 50 sieve plates; heatable through a double jacket IV. Test Procedure 1. Reaction The sodium sulfite solution adjusted with sulfuric acid to the desired pH value is initially introduced into the reactor and heated to the reaction temperature, after which the ether sulfate solution with a correspondingly adjusted pH value is introduced by means of the piston pump (see addition time). After the reaction (see reaction time), the reaction mixture is cooled to a temperature below 100° C. and subsequently worked up by extraction.

2. Extraction

The extraction tests were carried out with n-hexanol and pentanol (isomer mixture). The two alcohols are equivalent in their properties as extractants and in the extraction result.

The extraction tests were carried out at 80° C. because the depletion of the valuable product in the aqueous phase is promoted by elevated temperatures. In single-stage operation, ether sulfonate is depleted to less than 1% by weight in the raffinate so that there may even be no need for multistage extraction. By addition of salts, such as NaCl, Na₂SO₄ or ammonium acetate, the coalescence behavior of the system can be improved to such an extent that the phase separation times are shortened.

Test 1

The reaction mixture test 1 was continuously worked up in a 3 m extraction lift column with an internal diameter of 5 cm and 50 sieve plates. The throughput was 18 l/h, the ratio of feed to extractant 3.5 and the temperature 80° C. n-Hexanol was used as extractant. An extract having the following composition was obtained:

| | |
|---|---|
| Ether sulfonate: | 19% |
| Water: | 21% |
| Hexanol: | 53% |
| Impurities:* | 7% |

*Ether sulfate, nonionic surfactants, Na₂SO₄

Test 2

The reaction mixture from test 2 was discontinuously worked up in a single-stage extraction using pentanol (isomer mixture). To this end, the feed and extractant were initially introduced into a stirred reactor in a ratio of 10:1, heated to 80° C. and intensively stirred for 0.5 h (large phase interface). After phase separation, the two phases were separately run off. An extract having the following composition was obtained:

| | |
|---|---|
| Ether sulfonate: | 29% |
| Water: | 40% |
| Pentanol: | 22% |
| Impurities:* | 9% |

*Ether sulfate, nonionic surfactants, Na₂SO₄

Test 3

The reaction mixture from test 3 was discontinuously worked up in a single-stage extraction using n-hexanol. To this end, the feed and extractant were initially introduced into a stirred reactor in a ratio of 2.3:1 together with 2% NaCl, heated to 80°C. and intensively stirred for 0.5 h (large phase interface). After phase separation, the two phases were separately run off and the organic phase was washed with 7% water and 1% NaCl.

An extract having the following composition was obtained:

| | |
|---|---|
| Cl⁻: | 0.2% |
| SO₃²⁻: | — |
| SO₄²⁻: | 0.05% |
| LS8 sulfate: | 1.2% |
| LS8 sulfonate: | 13.6% |
| Nonionic surfactants: | 4.4% |

We claim:

1. The process of recovering oil from an oil reservoir, comprising preparing a surfactant mixture consisting essentially of an alkyl ether sulfonic acid or salt thereof as a principal constituent and at most a substantially equal quantity of alkoxylated alcohol as a by-product of the process by reacting an alkyl ether sulfate with an aqueous alkali metal sulfite solution at a temperature of from about 160° C. to about 220° C. a pH of from about 7.5 to about 10, and under a pressure of up to about 20 bar, wherein said alkali metal sulfite is present in a stoichiometric excess with respect to said alkyl ether sulfate, and wherein said alkyl ether sulfate is added to said aqueous alkali metal sulfite solution with simultaneous mixing at a rate so that about 20% of the total reaction time is taken up by the addition of said alkyl ether sulfate, and extracting the surfactant mixture formed with a substantially water-insoluble alcohol at a temperature of from about 50° C. to about 100° C. whereby said surfactant mixture is substantially free from sulfate salt, and flooding said oil reservoir with said surfactant mixture.

2. The process as in claim 1 wherein said alkyl ether sulfate contains from 6 to 18 carbon atoms in the alkyl radical and has an average degree of alkoxylation from about 1 to about 10.

3. The process as in claim 1 wherein said alkali metal sulfite is initially present in a molar ratio of up to about 5 with respect to said alkyl ether sulfate.

4. The process as in claim 1 wherein said reacting step is conducted at a temperature of from about 180° C. to about 200° C., at a pH from about 8 to about 9, and with a molar ratio of said alkali metal sulfite to said alkyl ether sulfate in the range from about 1.5 to about 2, whereby said surfactant mixture contains at least about 60% by weight of alkyl ether sulfonate, based on the weight of said surfactant mixture.

5. The process as in claim 1 including separating said water-insoluble alcohol from said surfactant mixture.

6. The process as in claim 1 wherein said surfactant mixture contains from about 15 to about 35% by weight of said water-insoluble alcohol, based on the weight of said surfactant mixture.

* * * * *